US006258542B1

(12) United States Patent
Hayashizaki (10) Patent No.: US 6,258,542 B1
(45) Date of Patent: Jul. 10, 2001

(54) METHOD FOR SUPPORTING DNA-FIXATION AND DNA-FIXED SUPPORT

(75) Inventor: Yoshihide Hayashizaki, Ibarakiken (JP)

(73) Assignee: The Institute of Physical and Chemical Resaerch (Riken), Saitama (JP)

( * ) Notice: Subject to any disclaimer, the term of this patent is extended or adjusted under 35 U.S.C. 154(b) by 0 days.

(21) Appl. No.: 09/388,917

(22) Filed: Sep. 2, 1999

(30) Foreign Application Priority Data

Sep. 4, 1998 (JP) .................................................. 10-250619
Aug. 27, 1999 (JP) .................................................. 11-240910

(51) Int. Cl.⁷ .............................. C12Q 1/68; C12P 19/34; C07H 21/01
(52) U.S. Cl. ............................ 435/6; 435/912; 536/24.3; 935/8; 935/77; 935/78
(58) Field of Search ..................... 435/6, 91.2; 536/24.3; 935/8, 77, 78

(56) References Cited

U.S. PATENT DOCUMENTS

| | | | |
|---|---|---|---|
| 4,626,501 | * | 12/1986 | Landes ...................................... 435/6 |
| 5,092,466 | * | 3/1992 | Anderson .............................. 206/438 |
| 5,955,266 | * | 9/1999 | Bray et al. ................................ 435/6 |

OTHER PUBLICATIONS

Sambrook et al., "Molecular Cloning. A laboratory manual", Second edition, pp. 7.46–7.48 and 9.34–9.41, 1989.*

* cited by examiner

Primary Examiner—Jeffrey Fredman
Assistant Examiner—Arun Chakrabarti
(74) Attorney, Agent, or Firm—Birch, Stewart, Kolasch & Birch, LLP.

(57) ABSTRACT

In order to make possible to preserve promptly and efficiently a DNA and to distribute the same without taking much labor and much time, a DNA solution is allowed to adhere to a sheet-like support having a prescribed thickness, and the DNA solution which has been allowed to adhere to the support is dried to fix the DNA onto the support.

28 Claims, 6 Drawing Sheets

M: MARKER DNA

DNA sequence ←—108

>gi|212271|gb|J00882|CHKLSZ1 Chicken egg white lysozyme gene: 5'-flank and exon-1
GCAGTCCCGCTGTGTGTACGACACTGGCAACATGAGGTCTTTGCTAATCTTGTGCTTTGCTTCCTGCCC
CTGGCTGCTCTGGGGAAAGTCTTTGACGATGTGAGCTGGCAGCGCTATGAAGCGTCACGGACTTGATA
ACTATCGGGGATACAGCCTGGGAAACTGTAAGTCTGTATTCTCAGGAGCACATGGGGTGG
GAATTCCATTT
>gi|212272|gb|J00883|CHKLSZ2 Chicken egg white lysozyme gene: exon-2
GCGCATCTTCATAAATAAGTCAGATACAGATTAAAATAATCTTTGAGGTTTTGTTTTCTTTTAAT
GGAACTTCGACAGGGTGTGTGCCGCAAAATTCGAGAGTAACTTCAACACCCAGGCTACAACCGTAACA
CCGATGGGAGTACCGACTACGGAATCCTACAGATCAACAGCCGCTGGTGTGCTGGTGCAACGATGGCAGGACCCC
AGGCTCCAGGAACCTGTGCAACATCCCGTGCTCAGGTGAGCTCAGTTTCTCAAGGCAACGAATGCCCTTC
CATATTCCGTGTGCAAGTAGA
>gi|212273|gb|J00884|CHKLSZ3 Chicken egg white lysozyme gene: exon-3
GCTTCCTTTCTTAAGCCCTGCTGAGCTCAGACACATAACAGCGAGCGTGAACTGCGCGAAGAAGATCGTCAG
CGATGGAAACGGCATGAACGCGTGGTAGGAGACGGGGG
>gi|212274|gb|J00885|CHKLSZ4 Chicken egg white lysozyme gene: exon-4 and 3' flank
TCTCCCTCCGCCCAGGGTCGCCTGGCGCAACCGCTGCAAGGCACCAGCGTCCAGGCGTGGATCAGAGGC
TGCCGGCTGTGAGGAGCTGCCGCACCCGGCCGCCCGCTGCACAGCCGCCGCTTGCGAGCGCGACGCT
ACCCGCTTGGCAGTTTTAAAGCATCCCTCATTAAAACGACTATACGCAAACGCCTT

Amino acid sequence

/translation="MRSLLILVLCFLPLAALGKVFGRCELAAAMKRHGLDNYRGYSLG
NWVCAAKFESNFNTQATNRNTDGSTDYGILQINSRWWCNDGRTPGSRNLCNIPCSALL
SSDITASVNCAKKIVSDGNGMNAWVAWRNRCKGTDVQAWIRGCRL" ←—110

○ cDNA library ←—112

FIG. 3C

FIG. 4 expected size 1.5kb

SEQUENCE LISTING

<160> NUMBER OF SEQ ID NOS: 7

<210> SEQ ID NO 1
<211> LENGTH: 222
<212> TYPE: DNA
<213> ORGANISM: Gallus gallus

<400> SEQUENCE: 1
gcagtcccgc tgtgtgtacg acactggcaa catgaggtct ttgctaatct tggtgctttg     60
cttcctgccc ctggctgctc tggggaaagt ctttggacga tgtgagctgg cagcggctat    120
gaagcgtcac ggacttgata actatcgggg atacagcctg ggaaactgta agtctgtatt    180
ctcatgattt ccagggagca catggggtgg gaatttccat tt                       222

<210> SEQ ID NO 2
<211> LENGTH: 301
<212> TYPE: DNA
<213> ORGANISM: Gallus gallus

<400> SEQUENCE: 2

-continued

```
gcgcatcttc ataaataagt cagatacaga tttaaaataa taatctttga gggttttgtt      60
ttcttttaat ggaacttcga caggggtgtg tgccgcaaaa ttcgagagta acttcaacac     120
ccaggctaca aaccgtaaca ccgatgggag taccgactac ggaatcctac agatcaacag     180
ccgctggtgg tgcaacgatg gcaggacccc aggctccagg aacctgtgca acatcccgtg     240
ctcaggtgag ctcagtttct caaggcaacg aatgcccttc catattccgt gtgcaagtag     300
a                                                                    301
```

<210> SEQ ID NO 3
<211> LENGTH: 109
<212> TYPE: DNA
<213> ORGANISM: Gallus gallus

<400> SEQUENCE: 3

```
gcttcctttc ttaagccctg ctgagctcag acataacagc gagcgtgaac tgcgcgaaga      60
agatcgtcag cgatggaaac ggcatgaacg cgtggtagga cgggggg                   109
```

<210> SEQ ID NO 4
<211> LENGTH: 197
<212> TYPE: DNA
<213> ORGANISM: Gallus gallus

<400> SEQUENCE: 4

```
tctccctccg cccagggtcg cctggcgcaa ccgctgcaag ggcaccgacg tccaggcgtg      60
gatcagaggc tgccggctgt gaggagctgc cgcacccggc ccgcccgctg cacagccggc     120
cgctttgcga gcgcgacgct acccgcttgg cagttttaaa cgcatccctc attaaaacga     180
ctatacgcaa acgcctt                                                    197
```

<210> SEQ ID NO 5
<211> LENGTH: 147
<212> TYPE: PRT
<213> ORGANISM: Gallus gallus

<400> SEQUENCE: 5

```
Met Arg Ser Leu Leu Ile Leu Val Leu Cys Phe Leu Pro Leu Ala Ala
  1               5                  10                  15

Leu Gly Lys Val Phe Gly Arg Cys Glu Leu Ala Ala Ala Met Lys Arg
                 20                  25                  30

His Gly Leu Asp Asn Tyr Arg Gly Tyr Ser Leu Gly Asn Trp Val Cys
             35                  40                  45

Ala Ala Lys Phe Glu Ser Asn Phe Asn Thr Gln Ala Thr Asn Arg Asn
         50                  55                  60

Thr Asp Gly Ser Thr Asp Tyr Gly Ile Leu Gln Ile Asn Ser Arg Trp
 65                  70                  75                  80

Trp Cys Asn Asp Gly Arg Thr Pro Gly Ser Arg Asn Leu Cys Asn Ile
                 85                  90                  95

Pro Cys Ser Ala Leu Leu Ser Ser Asp Ile Thr Ala Ser Val Asn Cys
                100                 105                 110

Ala Lys Lys Ile Val Ser Asp Gly Asn Gly Met Asn Ala Trp Val Ala
            115                 120                 125

Trp Arg Asn Arg Cys Lys Gly Thr Asp Val Gln Ala Trp Ile Arg Gly
        130                 135                 140

Cys Arg Leu
145
```

-continued

```
<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:primer M13

<400> SEQUENCE: 6
cagtcacgac gttgtaaaac gacggccagt                                       30

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:primer RV32

<400> SEQUENCE: 7
gataacaatt tcacacagga aacagctatg ac                                    32
```

METHOD FOR SUPPORTING DNA-FIXATION AND DNA-FIXED SUPPORT

BACKGROUND OF THE INVENTION

1. Field of The Invention

The present invention relates to a method for supporting DNA-fixation and a DNA-fixed support, and more particularly to a suitable method for supporting DNA-fixation and a DNA-fixed support used in case of utilizing DNAs in DNA technology industry, life science industry as well as medical and pharmaceutical industry etc.

Furthermore, a method for supporting fixation of RNA or PNA, or other high-molecular fragments with base sequences and a fixed support of RNA or PNA, or other high-molecular fragments with base sequences as well as to a method for delivering and storing DNA or RNA or PNA, or other high-molecular fragments with base sequences.

2. Description of The Related Art

Heretofore, either of a method wherein DNA in a state of aqueous solution is frozen as it stands, or a method wherein DNA is subjected to glycerol stock at −80° C. together with host cells in a state where the DNA is cloned into vector has been made in order to preserve stably DNA for a long period of time.

In the case where DNA which has been preserved by a conventional method as described above is intended to distribute by mailing or the like manner, for example, in the DNA which has been preserved by the former method (the DNA in a state of aqueous solution is frozen as it stands), the following steps must be taken. First, the solution of DNA which has been frozen is unfrozen to prepare a DNA aqueous solution. Thereafter, the resulting prepared DNA aqueous solution is pipetted into a micro-tube (a micro-tube is made of, for example, polypropylene and the like). Furthermore, the DNA aqueous solution which has been pipetted into the micro-tube is dried completely, and then the resulting dried DNA is mailed together with the micro-tube at ordinary temperature.

On one hand, in the DNA which has been preserved by the latter method (DNA is subjected to glycerol stock at −80° C. together with host cells in a state where the DNA is cloned into vector has been made), the following steps must be taken. First, the DNA is extracted from the host cells, and an aqueous solution of the DNA is prepared. After having been prepared the DNA aqueous solution, the resulting prepared DNA aqueous solution is pipetted into a micro-tube, and then the DNA aqueous solution which has been pipetted into the micro-tube is dried completely, thereafter the resulting dried DNA is mailed together with the micro-tube at ordinary temperature as in the case of the former method described above.

Namely, a variety of processes of operation which require comparatively long working hours such as preparation of DNA aqueous solution, pipetting of the DNA aqueous solution into a micro-tube, and drying of the DNA aqueous solution which has been pipetted into the micro-tube must have been carried out in the case where DNA preserved by the above described conventional methods is intended to distribute widely by mailing or the like manner.

In these circumstances, although small number of micro-tubes can be distributed by small number of work force, an amount of working becomes enormous in the case where the number of micro-tubes to be distributed increases, so that there is such a problem that much labor and much time are required, resulting in difficulty in distribution of such micro-tubes as a matter of fact.

Recently, on the other hand, further plenitude of DNA bank system is requested with the development of genome analysis project of a variety of organisms, so that a need for reductions of the labor and time as described above as well as a need for engineering developments for the sake of increased efficiency in operation which are required for preservation and distribution of DNA become remarkable.

Moreover, there are also such problems and needs as described above as to RNA or PNA, or other high-molecular fragments with base sequences.

OBJECTS AND SUMMARY OF THE INVENTION

The present invention has been made in view of the above described problems involved in the prior art and a need for solving such problems in late years.

Accordingly, an object of the present invention is to provide a method for supporting DNA-fixation and DNA-fixed support by which DNA can be promptly and efficiently preserved and distributed without taking much labor and much time.

Another object of the present invention is to provide a method for supporting fixation of RNA or PNA or other high-molecular fragments with base sequences and a fixed support of RNA or PNA or other high-molecular fragments with base sequences by which RNA or PNA or other high-molecular fragments with base sequences can be promptly and efficiently preserved and distributed without taking much labor and much time.

A further object of the present invention is to provide a method for delivering and storing DNA or RNA or PNA or other high-molecular fragments with base sequences.

In order to attain the above described object, a method for supporting DNA-fixation according to the present invention is constituted in such that a DNA solution is allowed to adhere to a sheet-like support having a prescribed thickness, or the DNA solution is allowed to adhere to the sheet-like support by printing, and the DNA solution which has been thus allowed to adhere to the support is dried, whereby the DNA is fixed to the support.

Namely, according to the method for supporting DNA-fixation of the present invention, DNA can be fixed or printed on a sheet-like support by such a simple operation that a DNA solution is allowed to adhere to a sheet-like support, and then the resulting sheet is dried, so that it becomes possible to preserve and distribute promptly and efficiently the DNA without taking much labor and much time.

Furthermore, a DNA-fixed support according to the present invention comprises a sheet-like support having a prescribed thickness, and a DNA fixed or printed to the support by drying a DNA solution which has been allowed to adhere to the support, or printing the DNA solution onto the support.

Thus, according to the DNA-fixed support of the present invention, since a DNA has been fixed or printed onto a sheet-like support, the resulting DNA-fixed support which is a support on which the DNA has been fixed or printed may be mailed without requiring any further treatment. As a result, it becomes possible to distribute promptly and efficiently without taking much labor and much time.

Under the circumstances, the above described support may be prepared from a material containing a site in which a DNA has been fixed or printed, the site being severable.

According to the preparation as described above, since a site in which a DNA has been fixed or printed can be severed, workability in recovering operation of the DNA which has been fixed or printed to the support can be improved.

Furthermore, the above described support may be prepared from cellulose as the major component.

According to the preparation as described above, a DNA fixed or printed to the support can be reliably preserved at ordinary temperature.

Moreover, the above described support may contain a site on which information as to a DNA which has been fixed or printed to the support is described.

According to the preparation as described above, contents of the DNA which has been fixed or printed to a support for DNA-fixation can be confirmed by visual observation of the DNA-fixed support.

Still further, a plurality of the above described supports are laminated to form a booklet, and a DNA may be fixed or printed to each support from which the above described booklet is formed.

According to the preparation as described above, a plurality of DNAs can be promptly and efficiently distributed by mailing the resulting booklet without taking much labor and much time.

Yet further, a DNA which has been fixed or printed to the above described support is arranged in such that the DNA is recovered by elution from the support.

Accordingly, the DNA which has been fixed or printed to the support can be easily recovered.

Still further, the DNA which has been recovered by elution from the above described support is arranged to be amplified by polymerase chain reaction.

In this case, a primer for polymerase chain reaction is supplied in the form of dots, powder or liquid.

It is to be noted that the fixed support of RNA or PNA or other high-molecular fragments with base sequences according to the present invention is an alternative substance of the above described DNA-fixed support of the present invention.

Furthermore, it is to be noted that the method for supporting fixation of RNA or PNA or other high-molecular fragments with base sequences according to the present invention is the one wherein RNA or PNA or other high-molecular fragments with base sequences are alternatively used in place of the DNA in the above described method for supporting DNA fixation.

Moreover, it is to be noted that the method for delivering and storing a DNA, or RNA or PNA or other high-molecular fragments with base sequences according to the present invention is the one wherein the DNA, or RNA or PNA or the other high-molecular fragments with base sequences are delivered or stored in the form of the above described DNA-fixed support of the invention, or of the above described fixed support of the RNA or PNA or the other high-molecular fragments with base sequences of the invention, respectively.

BRIEF DESCRIPTION OF THE DRAWINGS

The present invention will become more fully understood from the detailed description given hereinbefore and the accompanying drawings which are given by way of illustration only, and thus are not limitative of the present invention, and wherein.

DETAILED DESCRIPTION OF THE PREFERRED EMBODIMENTS

In conjunction with the accompanying drawings, an example of preferred embodiments of the method for supporting DNA-fixation and the DNA-fixed support as well as of the method for supporting fixation of RNA or PNA or the other high-molecular fragments with base sequences and the fixed support of RNA or PNA or other high-molecular fragments with base sequences, and the method for delivering and storing DNA or RNA or PNA or other high-molecular fragments with base sequences according to the present invention, respectively, will be described in more detail hereinafter.

Figure 1:
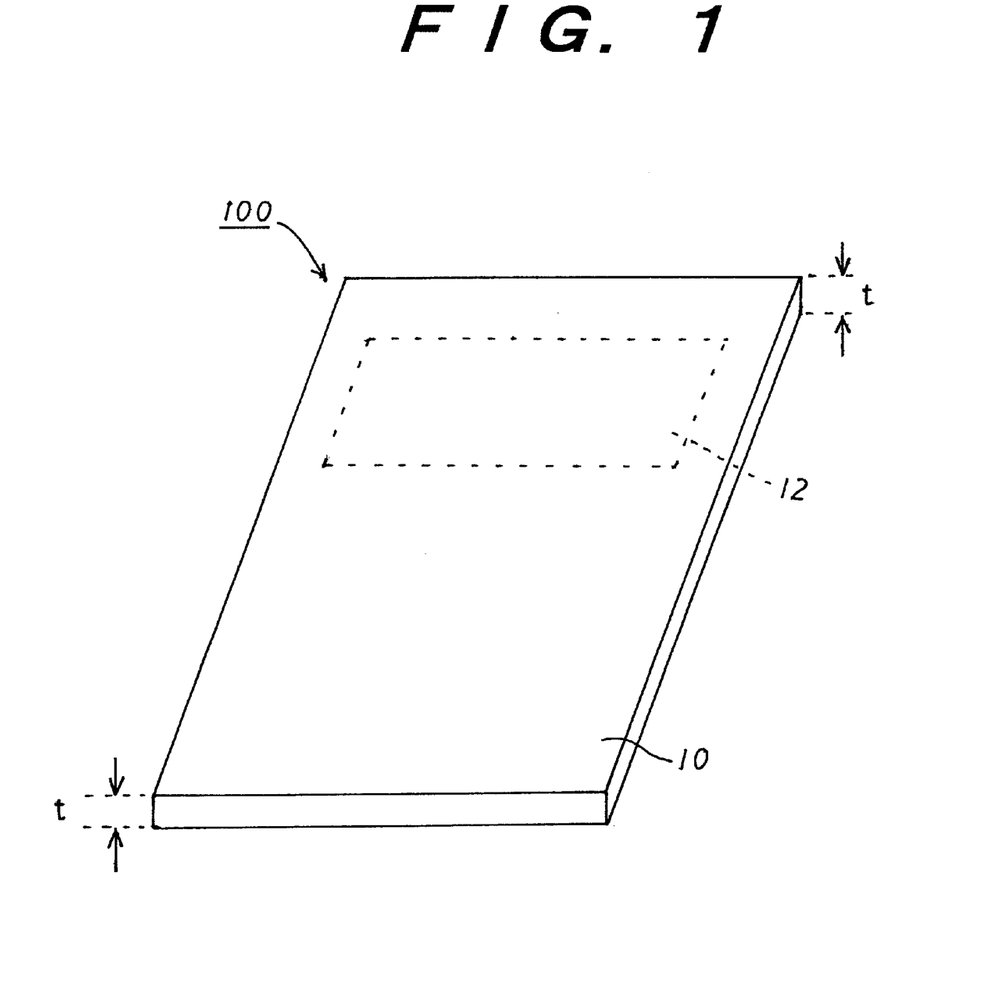
FIG. 1 is a conceptual explanatory view for describing an example of preferred embodiments of a method for supporting DNA-fixation according to the present invention.

First, an example of preferred embodiments of the method for supporting DNA-fixation will be described by referring to FIG. 1. The method for supporting DNA-fixation according to the present invention is constituted in such that a DNA solution such as a DNA aqueous solution is allowed to adhere to a sheet-like support 10 having a thickness t, and the DNA solution which has been allowed to adhere to the support 10 is dried to fix the DNA to the support 10.

Reference numeral 12 designates conceptually the DNA which has been fixed to the support 10, and it is referred to as a DNA-fixed support 100.

In this case, a material manufactured from cellulose as the major component, more specifically, an ordinary plain paper copy (PPC) and the like may be used as the support 10.

Furthermore, a material prepared by coating cellulose on another sheet to reinforce the sheet with a film-like cellulose may be used as the support 10. In this case, it is preferred that a DNA solution is allowed to adhere to the coated cellulose film of the support 10.

On one hand, it may be arranged in such that the surface of the support 10 to which the DNA 12 has been fixed is coated with a plastic or the like to reinforce the support 10.

The DNA-fixed support 100 manufactured as described above can be preserved at ordinary temperature so that it can be easily stored as is apparent from an experiment by the present applicant which will be described later.

A thickness t of the support 10 may be, for example, 1 mm or less. When the thickness t is made to be very thin thickness, for example, around 0.1 mm, its workability is improved even if a number of DNA-fixed supports 100 are stacked for distributing them, because they are not so bulky.

Figure 2:
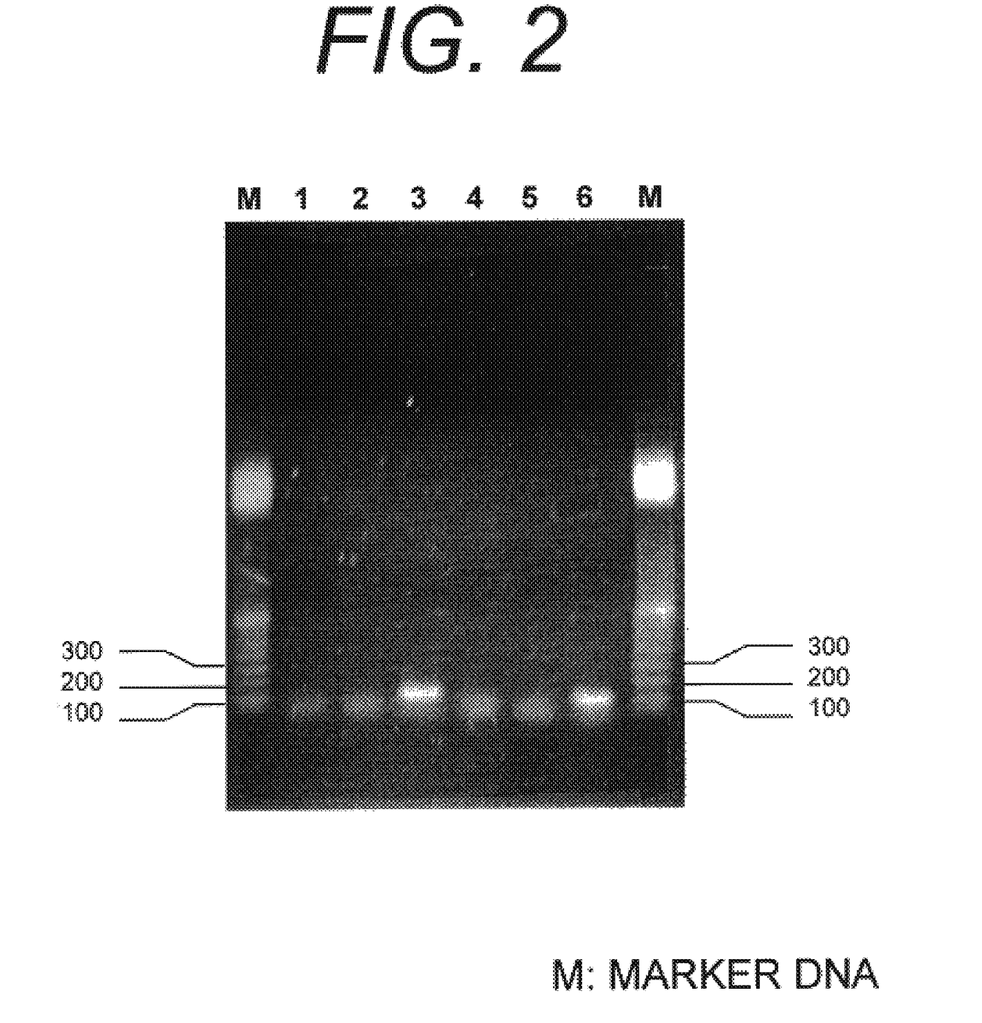
FIG. 2 is a photograph for electrophoresis which indicates experimental results made by the present applicant.

FIG. 2 is a photograph for electrophoresis indicating experimental results made by the present applicant. The experiment will be described herein by referring to FIG. 2 together with FIG. 1.

First, a DNA solution (200 ng/$\mu$L) is allowed to adhere to each of a glass micro-fiber filter as a support 10 and an ordinary plain paper copy as a support 10 by dropping 1 $\mu$L each of the DNA solution, and the resulting supports are dried at 50° C. for 30 minutes to prepare each of DNA-fixed supports 100, respectively.

The DNA-fixed supports 100 (glass micro-fiber filter and ordinary PPC) thus prepared are allowed to stand at ordinary temperature.

With respect to the DNA-fixed supports 100 (glass micro-fiber filter and ordinary PPC), recovery of the DNA 12 which has been fixed to each support 10 was carried out by immersing each of the DNA-fixed supports 100 into 100 µL of 50 mM Tris-Cl buffer solution (pH 7.5) at room temperature for 30 minutes, and 35 µL of the recovered solution was subjected to polymerase chain reaction (PCR) as a template DNA solution, whereby the DNA was amplified.

In order to confirm results of recovery from and amplification of the DNA 12 in the DNA-fixed supports 100 (glass micro-fiber filter and ordinary PPC), electrophoresis was made with the use of 1.0% agarose.

The above described photograph for electrophoresis shown in FIG. 2 indicates such experimental results wherein the results in the case where a glass micro-fiber filter is used as the support 10 are shown in lane 1, lane 2, lane 4, and lane 5, respectively, while the experimental results in the case where an ordinary PPC is used as the support 10 are shown in lane 3 and lane 6, respectively.

It is to be noted that two M lanes positioned at the opposite ends of the photograph in FIG. 2 with interposing lane 1 through lane 6 between these M lanes are marker DNA each indicating a length of DNA. In FIG. 2, the lowermost object is a double strand DNA composed of 100 nucleic acid base pairs, and thereafter 100 bases each longer DNA are successively aligned upwards.

In this case, a length to be amplified in the DNA used is 153 nucleic acid base pairs, and the amplification of DNA corresponding thereto is observed only in lane 3 and lane 6.

More specifically, it has been found in accordance with the above described experimental results that the DNA 12 fixed to the support 10 in the DNA-fixed support 100 prepared by the use of an ordinary PPC or the like manufactured from cellulose as the support 10 can be preserved at ordinary temperatures, besides, the DNA 12 fixed to the support 10 can be recovered by elution from the support 10 in the DNA-fixed support 100, and in addition, the DNA 12 thus recovered by elution can be amplified by polymerase chain reaction.

For the sake of allowing to adhere the DNA 12 to the support 10, the following procedures may be adopted, namely, they are the one wherein DNA is picked up by the use of a pin, and the DNA on the pin is further transferred to the support 10, a procedure wherein a DNA solution contained in a syringe is dropped onto the support 10 to adhere the DNA thereto, and a procedure wherein a DNA solution is allowed to adhere to the support 10 in a printed state by utilizing an existing printing technique.

In this case, for example, such a printing technique of ink-jet printing system which is applied to ink-jet printer and the like may be utilized as the existing printing system.

In order to apply a printing technique of ink-jet printing system, a DNA solution is used in place of a coloring matter such as a printing ink, and the support 10 corresponding to a printing paper may be printed by the use of the DNA solution in accordance with ink-jet printing system.

Thus, the existing printing technique can be very easily applied to a method for supporting DNA-fixation according to the present invention in such a point that a DNA solution can be used in place of a printing ink without any modification in accordance with ink-jet printing system wherein a piezo-electric element or a heat-producing element is utilized.

In a printing technique of ink-jet printing system, dots each having around 20 µm to 100 µm dimension can be usually printed, so that it becomes possible to allow a DNA solution to adhere to a support in a high density.

Moreover, DNA in a dried state is stable unlike other biomolecules such as protein, and it can withstand sufficiently a temperature of around 100° C., so that an electronic printing or thermal transfer type printing technique including that actualized by laser printer can be also applied to the method for supporting DNA-fixation according to the present invention.

Figure 3A:
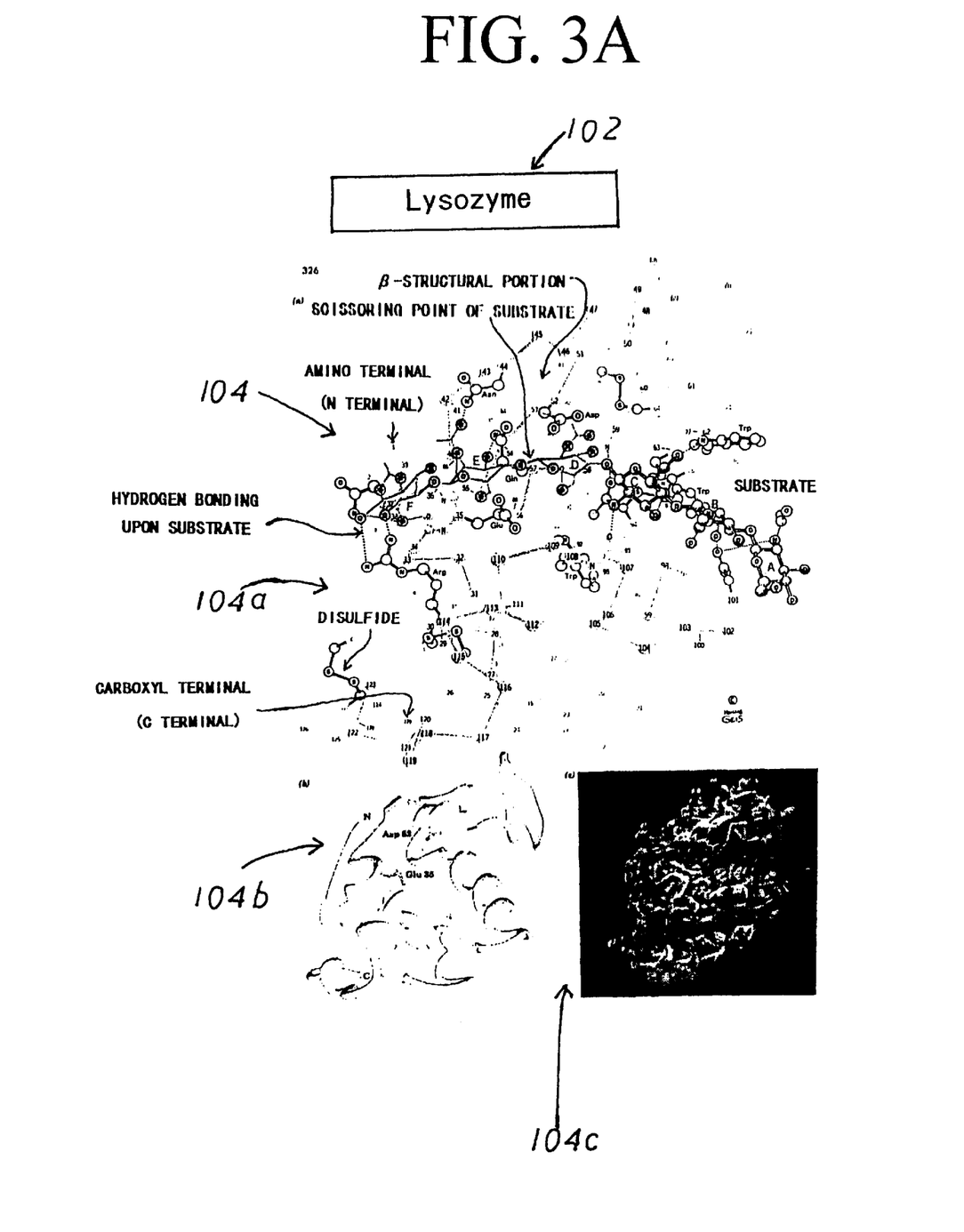
FIGS. 3A, 3B, and 3C are explanatory views showing an example of preferred embodiments of a DNA-fixed support according to the present invention.
Figure 3B:
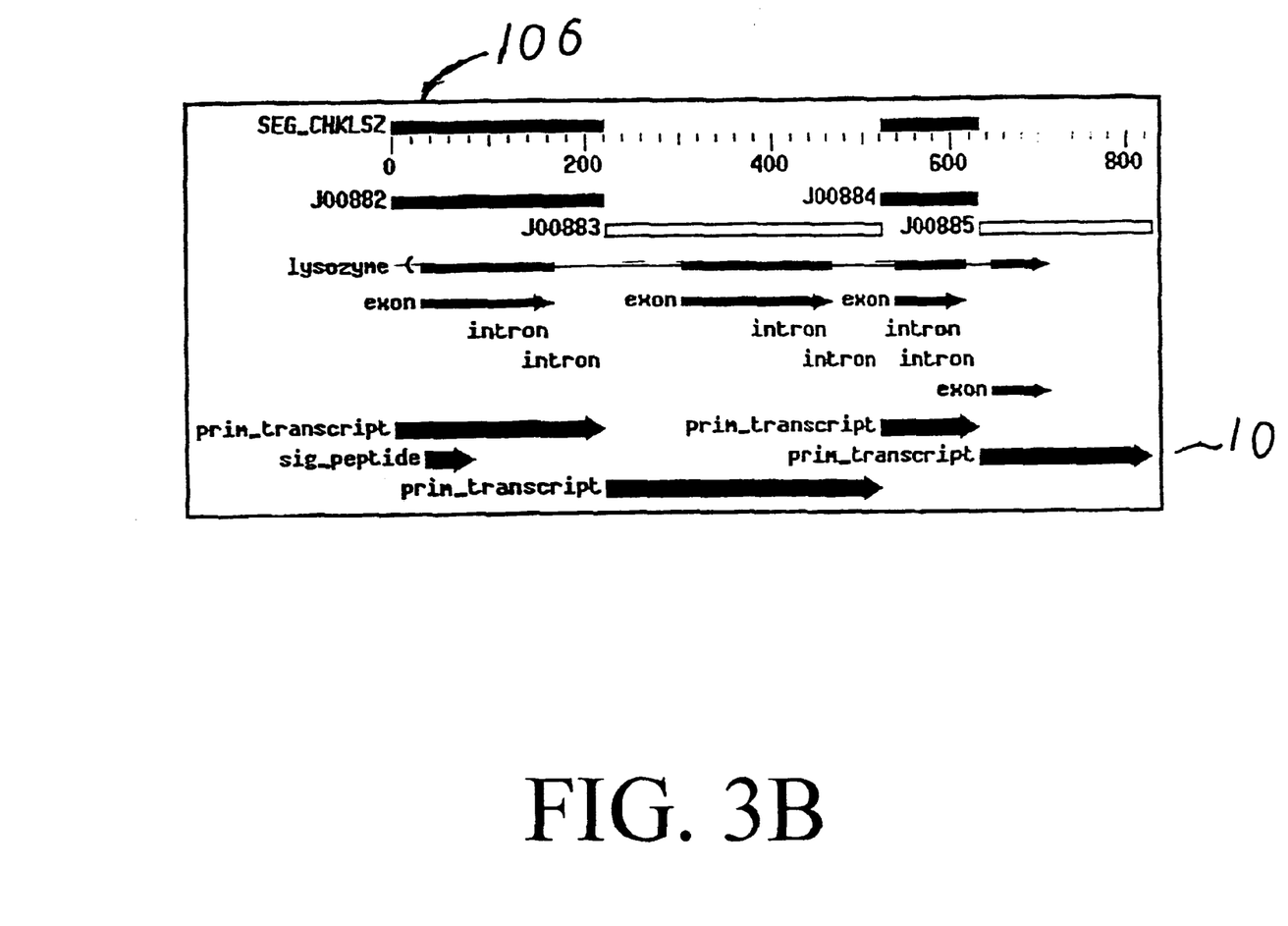
Figure 3C:
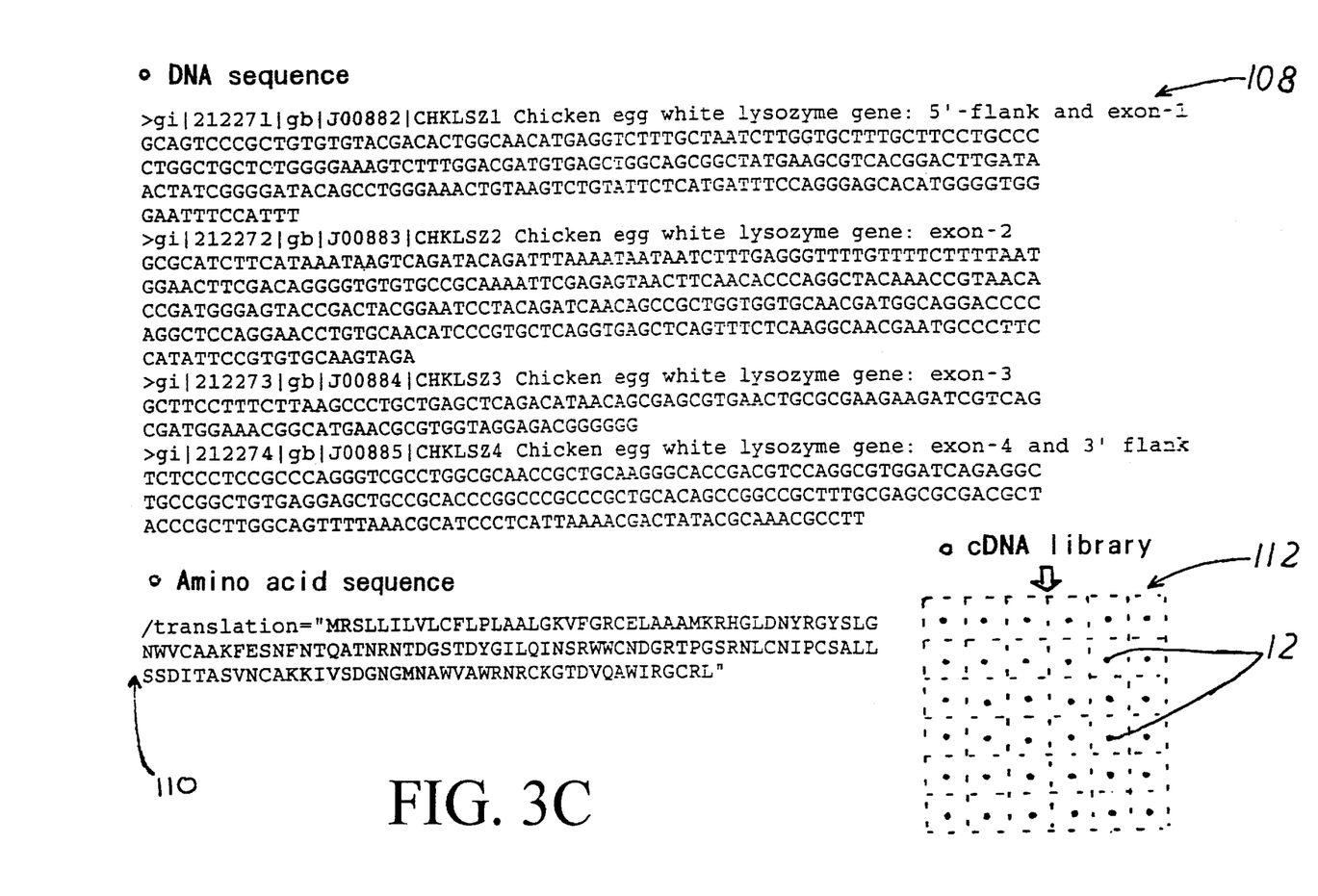

FIG. 3 shows an example of a preferred embodiments of a DNA-fixed support 100 according to the present invention which is prepared by fixing a DNA 12 to a support 10 in accordance with a method for supporting DNA-fixation of the present invention.

In the DNA-fixed support 100, a name description area 102 is prepared in a left upper site on the DNA-fixed support 100, and a name of protein coded by the DNA is written in the name description area 102. In an example shown in FIG. 3, "Lysozyme" has appeared in the name description area 102.

Furthermore, a structure description area 104 is prepared in a site below the name description area 102 of the DNA-fixed support 100. In an example shown in FIG. 3, a structure of a protein is described by three types of describing manners wherein reference characters 104a, 104b, and 104c designate the structures of the protein described in accordance with different describing manners, respectively.

The structures designated by reference characters 104b and 104c show solid figures obtained from computer images.

Moreover, a positional description area 106 is prepared in a right upper site on the DNA-fixed support 100, and a positional of each exon in lysozyme on genome is indicated in the layout description area 106.

In a lower site of the positional description area 106, base sequences (DNA sequence) description area 108 is prepared, and actual base sequences of each exon are described in the base sequence description area 108.

In addition, an amino acid sequence description area 110 is prepared in a lower site of the base sequence description area 108, and amino acid sequence of lysozyme is described in the amino acid sequence description area 110.

In case of such protein which has been modified after translation, it is desirable to describe also the information relating thereto in the amino acid sequence (SEQ ID NO:5) description area 110.

In the right bottom site in the DNA-fixed support 100, a DNA spotting area 112 is prepared as a DNA fixed area. In the DNA spotting area 112, the DNA 12 is fixed by the above described method for supporting DNA-fixation according to the present invention.

In FIG. 3, each dot existing in a rectangle drawn by a broken line in the DNA library area 112 depicts the DNA 12.

In the example of FIG. 3, the DNA 12 represents cDNA of lysozyme.

It may be arranged in such that the DNA-fixed supports 100 as shown in FIG. 3 are prepared in every DNA, and they are put together by laminating them to obtain a booklet.

Such booklet can be easily delivered and stored as in the case of the single DNA-fixed support 100.

It is not necessarily required that DNA should be fixed or printed in a restricted DNA spotting area 112 which has been previously prepared, but it may be, for example, printed partly or wholly with the use of the DNA itself in the name description area 102.

In the example shown in FIG. 3, although a variety of information contained in the name description area 102, the structure description area 104, the positional description area 106, the base sequence description area 108, and the amino acid sequence description area 110 have been prepared all together in the DNA-fixation support 100, it is not limited thereto, but separate volumes composed of a document of the DNA-fixed support 100 and another document containing areas of a variety of information relating to the name description area 102, the structure description area 104, the positional description area 106, the base sequence description area 108, and the amino acid sequence description area 110 may be prepared.

Moreover, in the case where separate volumes composed of the DNA-fixed support 100 and another document containing areas of a variety of information are described as mentioned above, it may be arranged in such that only the DNA-fixed supports 100 relating to respective DNAs are put together, and at the same time, only a document containing areas of a variety of information are described is put together, respectively.

In case of putting only the DNA-fixed supports 100 relating to respective DNAs together, they are easily managed by indicating such effect that a certain DNA-fixed support 100 belongs to which DNA (with, for example, numbering or the like manner).

In case of employing DNAs 12 which have been fixed in the DNA spotting area 112 of the DNA-fixed support 100, a DNA 12 indicated by each dot in each area shown by a broken line in the DNA spotting area 112 is cut off with scissors, a cutter and the like, the piece of the DNA-fixed support thus cut off is transferred to a micro-test tube, and it may be amplified under ordinary conditions by polymerase chain reaction.

In this case, a primer for polymerase chain reaction may be supplied in the form of dots, or powder or liquid.

In case of a booklet which has been prepared by laminating DNA-fixed supports 100, a primer in the form of dots may be placed in anywhere in any page, or may be added to the end of the booklet as an appendix.

On one hand, even if there are various types of DNAs, it is also possible to supply a primer in the form of liquid or dry powder by containing such primer in an ampoule or a small test tube in such a case where a common primer may be used in a certain extent so that the number of types of primer may be reduced.

Figure 4:
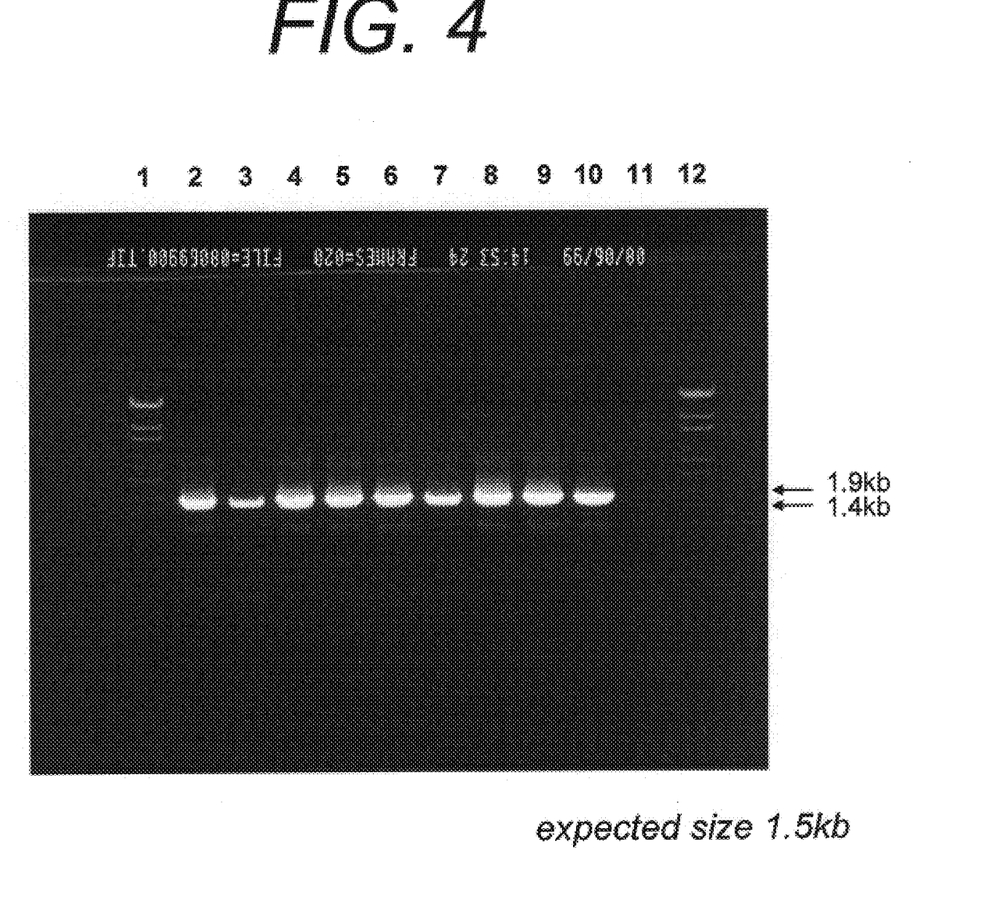
FIG. 4 is a photograph of electrophoresis showing results of the experiment performed by the present applicant.

In the following, experimental results by the present applicant with respect to recovery (check in reproducibility) of a DNA which has been fixed to a variety of sheets and influence of an ink upon the recovery will be described by referring to a photograph of electrophoresis indicating the experimental results by the present applicant shown in FIG. 4.

First, various types of sheets each having 5 mm×5 mm size (A) as well as having 10 mm×10 mm size (B) were prepared.

Further, 333 ng/$\mu$l of plasmid DNA (prepared by inserting 1.5 kb of $\lambda$ DNA fragment in pBS at a site of EcoRV) (H solution) and 333 ng/$\mu$l of 17% (v/v) solution containing a fountain pen ink (F solution) were prepared as DNA samples.

Then, 3 $\mu$l (1 $\mu$g) each of the H solution or the F solution was spotted on a sheet having the size (A), while 6 $\mu$l (2 $\mu$g) each of the solutions was spotted on a sheet having the size (B), and these sheets were dried at 65° C. for 30 minutes, respectively. Thereafter, the sheet having the size (A) was immersed into 200 $\mu$l of water, while the sheet having the size (B) was immersed into 300 $\mu$l of water, respectively. These immersed sheets were dried at 65° C. for 10 minutes, and further they were treated at room temperature for 2 hours thereby to conduct elution.

Phenol extraction (extracting two times with use of phenol:chloroform:isoamyl alcohol=25:24:1) was repeated upon an eluate, and then the DNA was recovered by ethanol precipitation method.

The resulting DNA was dissolved in 10 $\mu$l of water, and PCR was conducted as follows. After the first reaction at 94° C. for 3 minutes, forty cycles of the reaction were repeated at 94° C. for 1 minute and 68° C. for 2 minutes with a final reaction volume: 25 $\mu$l, a reaction composition: M13 (SEQ ID NO:6) primer (M3-30: 0.5 $\mu$l of 10 $\mu$M 5'-CAGTCACGACGTTGTAAAACGACGGCCAGT-3', 0.5 $\mu$l of 10 $\mu$M RV32 (SEQ ID NO:7): 5'-GATAACAATTTCACACAGGAAACAGCTATGAC-3'), 2.5 $\mu$l of ExTaq 10×buffer solution, 2 $\mu$l of 2.5 mM dNTP, 1 unit of ExTaq, and DNA (which will be indicated hereinafter).

After the reaction, 5 $\mu$l of the reaction product was subjected to 1% agarose electrophoresis to detect (about 1.5 kbp of) a PCR product. The results are shown in FIG. 4.

Lane 1 is a DNA size marker ($\lambda$/StyI 200 $\mu$g), lane 2 shows the one obtained by spotting the F solution onto a medical paper having the size (A), lane 3 shows the one obtained by spotting the F solution onto a medical paper having the size (B), lane 4 indicates the one obtained by spotting the F solution onto a copy paper having the size (A), lane 5 shows the one obtained by spotting the F solution onto a copy paper having the size (B), lane 6 shows the one obtained by spotting the H solution onto a medical paper having the size (A), lane 7 shows the one obtained by spotting the H solution onto a medical paper having the size (A), lane 8 shows the one obtained by spotting the H solution onto a copy paper having the size (A), lane 9 shows the one obtained by spotting the H solution onto a copy paper having the size (B), lane 10 is the one with no sheet (positive control), lane 11 is the one with no sheet (negative control), and lane 12 is a DNA size marker ($\lambda$/StyI 200 $\mu$g).

Three $\mu$l of a DNA was applied to the lane 2, lane 3, and lane 6, respectively, while 1/50 $\mu$l of the DNA was applied to the lane 4, lane 5, lane 7, lane 8, and lane 9, respectively.

Hence, according to the method for supporting DNA-fixation and the DNA-fixed support of the present invention, a DNA-fixed support according to the invention can be prepared from a part of an original DNA while preserving stably the original DNA in a state of aqueous solution for a long period of time by a conventional manner such as refrigeration, so that it becomes possible to preserve promptly and efficiently the DNA, besides to distribute as well as to store the same without taking much labor and much time.

More specifically, according to the method for supporting DNA-fixation and the DNA-fixed support of the present invention, it is possible that a DNA solution is used in place of a coloring matter in an existing printing technique, and the DNA solution for distribution use is allowed to adhere promptly and efficiently to a support 10 such as a printing paper or the like as described above, whereby a number of DNA-fixed supports for distribution use which can be mailed are prepared.

When it is supposed that, for example, 1000 types of DNAs can be fixed to a single support 10 by an existing printing technique, the whole cDNAs in a mouse may be contained in a booklet having about 100 pages, because the total number of cDNAs in mouse is about a hundred thousand in species (corresponding to the total number of proteins which can be translated from mouse genes). A booklet of around 100 pages can be mailed and stored easily.

On the other hand, it is impossible as a matter of fact in view of much labor and much time to effect usually distribution of samples of a hundred thousand DNAs by the manner described in the paragraph "Description of The Related Art". In this respect, increased efficiency in operation involved in the method for supporting DNA-fixation and the DNA-fixed support according to the present invention is remarkable.

Moreover, according to the method for supporting DNA-fixation and the DNA-fixed support of the present invention, it becomes possible to attach related DNA molecules themselves to a document in which a variety of information as to functions of the DNAs and proteins have been described as shown in FIG. 3.

Besides, a user who has received a booklet which had been prepared by laminating the DNA-fixed supports 100 as shown in FIG. 3 selects DNAs to be used on the basis of a variety of information contained in the booklet received, and the user can cut off necessary ones among the various attached DNAs in each DNA-fixed support 100 in which DNAs have been printed. Accordingly, it becomes possible to use information of DNAs together with the corresponding DNA molecules themselves in a close relationship.

It is to be noted that although the DNAs which have been fixed to a distributed DNA-fixed support 100 can be used by eluting the DNAs therefrom as they are, it is rather usual that the DNA 12 which has been fixed to the DNA-fixed support 100 is amplified as a template for polymerase chain reaction, and then, the resulting amplified product is served for a variety of applications.

According to the method for supporting DNA-fixation and the DNA-fixed support of the present invention, it results in such an advantage for making a relationship between supply and demand in a variety of DNA industries more intimate. Therefore, it becomes possible to establish more prompt and more efficient preparations for research and development.

While DNA has been described in the above described preferred embodiments, the DNA may be replaced, as a matter of course, by RNA or PNA or other high-molecular fragments with base sequences.

Since the present invention has been constituted as described above, there are excellent advantages in that DNAs can be preserved and distributed promptly and efficiently without taking much labor and much time.

Furthermore, since the present invention has been constituted as described above, there are excellent advantages in that DNA or RNA or PNA or other high-molecular fragments with base sequences can be preserved and distributed promptly and efficiently without taking much labor and much time.

Moreover, since the present invention has been constituted as described above, there are excellent advantages in that DNA or RNA or PNA or other high-molecular fragments with base sequences can be easily delivered and stored without taking much labor and much time.

It will be appreciated by those of ordinary skill in the art that the present invention can be embodied in other specific forms without departing from the spirit or essential characteristics thereof.

The presently disclosed embodiments are therefore considered in all respects to be illustrated and not restrictive. The scope of the invention is indicated by the appended claims rather than the foregoing description, and all changes that come within the meaning and range of equivalents thereof are intended to be embraced therein.

The entire disclosure of Japanese Patent Application No. 10-250619 filed on Sep. 4, 1998 and Japanese Patent Application No. 11-240910 filed on Aug. 27, 1999 including specification, claims, drawings and summary are incorporated herein by reference in its entirety.

What is claimed is:

1. A method for supporting RNA-, PNA-, other high molecular fragment- or DNA-fixation or printing, comprising: directly applying or adhering a RNA, PNA, other high molecular fragment or DNA solution to a sheet-like support having a prescribed thickness, and drying the RNA, PNA, other high molecular fragment or DNA solution, thereby fixing or printing the RNA, PNA, other high molecular fragment or DNA to said support, wherein a plurality of said supports are laminated to form a booklet, and a RNA, PNA, other high molecular fragment or DNA has been fixed or printed to each support from which said booklet is to be formed.

2. A RNA-, PNA-, other high molecular fragment- or DNA-fixed support, comprising:

a sheet-like support having a prescribed thickness, and a RNA, PNA, other high molecular fragment or DNA prepared by drying a RNA, PNA, other high molecular fragment or DNA solution which has been directly adhered or applied to said support thereby fixing or printing the DNA to said support, wherein a plurality of said supports are laminated to form a booklet, and a RNA, PNA, other high molecular fragment or DNA has been fixed or printed to each support from which said booklet is to be formed.

3. An RNA-, PNA-, other high molecular fragment- or DNA-fixed support as claimed in claim 2, wherein:

said support is prepared from a material containing a site to which a RNA, PNA, other high molecular fragment or DNA has been fixed or printed, the site being severable.

4. An RNA-, PNA-, other high molecular fragment- or DNA-fixed support as claimed in claim 2, wherein:

said support is prepared with cellulose as the major component.

5. An RNA-, PNA-, other high molecular fragment- or DNA-fixed support as claimed in claim 2, wherein:

said support contains a site in which information relating to the RNA, PNA, other high molecular fragment or DNA which has been fixed or printed to said support is described.

6. An RNA-, PNA-, other high molecular fragment- or DNA-fixed support as claimed in claim 4, wherein:

said support contains a site in which information relating to the RNA, PNA, other high molecular fragment or DNA which has been fixed or printed to said support is described.

7. An RNA-, PNA-, other high molecular fragment- or DNA-fixed support as claimed in claim 4, wherein:

a plurality of said supports are laminated to form a booklet, and an RNA, PNA, other high molecular fragment or DNA has been fixed or printed to said support from which the booklet is to be formed.

8. An RNA-, PNA-, other high molecular fragment- or DNA-fixed support as claimed in claim 5, wherein:

a plurality of said supports are laminated to form a booklet, and an RNA, PNA, other high molecular fragment or DNA has been fixed or printed to said support from which the booklet is to be formed.

9. An RNA-, PNA-, other high molecular fragment- or DNA-fixed support as claimed in claim 6, wherein:

a plurality of said supports are laminated to form a booklet, and an RNA, PNA, other high molecular fragment or DNA has been fixed or printed to said support from which the booklet is to be formed.

10. The method as claimed in claim 1, wherein:

the RNA, PNA, other high molecular fragment or DNA which has been fixed or printed to said support is recovered by elution from said support.

11. The method as claimed in claim 1, wherein:

the RNA, PNA, other high molecular fragment or DNA which has been fixed or printed to said support is recovered by elution from said support and wherein said support is prepared with cellulose as the major component.

12. The method as claimed in claim 1, wherein:

the RNA, PNA, other high molecular fragment or DNA which has been fixed or printed to said support is recovered by elution from said support and wherein said support contains a site in which information relating to the DNA which has been fixed or printed to said support is described.

13. The method as claimed in claim 1, wherein:
the RNA, PNA, other high molecular fragment or DNA which has been fixed or printed to said support is recovered by elution from said support and wherein said support contains a site in which information relating to the DNA which has been fixed or printed to said support is described and said support is prepared with cellulose as the major component.

14. The method as claimed in claim 11, wherein the RNA, PNA, other high molecular fragment or DNA which has been recovered by elution from said support is amplified by polymerase chain reaction.

15. The method as claimed in claim 12, wherein the RNA, PNA, other high molecular fragment or DNA which has been recovered by elution from said support is amplified by polymerase chain reaction.

16. The method as claimed in claim 13, wherein the RNA, PNA, other high molecular fragment or DNA which has been recovered by elution from said support is amplified by polymerase chain reaction.

17. The method as claimed in claim 14, wherein the RNA, PNA, other high molecular fragment or DNA which has been recovered by elution from said support is amplified by polymerase chain reaction.

18. The method of as claimed in any one of claim 2, claim 3, claim 4, claim 5, claim 6, claim 7 and claim 8, wherein:
a primer for polymerase chain reaction is supplied in the form of dots, powder or liquid.

19. In the method for supporting DNA-fixation as claimed in claim 1,
a method for supporting fixation of RNA PNA or other high-molecular fragments with base sequences wherein:
said RNA or PNA or other high-molecular fragments with base sequences are used in place of said DNA.

20. A method for delivering or storing DNA, RNA, PNA or other high-molecular fragments with base sequences, comprising,
delivering or storing said DNA, RNA, PNA or other high-molecular fragments with base sequences as a sheet-like support having a prescribed thickness, and a DNA, RNA, PNA or other high-molecular fragments with base sequences prepared by directly applying or adhering a solution of said DNA, RNA, PNA or other high-molecular fragments with base sequences to said sheet-like support and drying said solution, thereby fixing or printing the DNA to said support,
wherein a plurality of said supports are laminated to form a booklet, and
a DNA, RNA, PNA or other high-molecular fragments with base sequences has been fixed or printed to each support from which said booklet is to be formed.

21. The method of claim 1, wherein the DNA, RNA, PNA or other high-molecular fragments with base sequences solution is applied or adhered directly to the support with a pin, syringe, or ink-jet printer.

22. The method of claim 1, wherein the DNA, RNA, PNA or other high-molecular fragments with base sequences solution is applied or adhered directly to the support using an electronic printing or thermal transfer printing.

23. The method of claim 19, wherein the solution of DNA, PNA, RNA or other high-molecular fragments with base sequences is applied or adhered directly to the support with a pin, syringe, or ink-jet printer.

24. The method of claim 19, wherein the solution of DNA, PNA, RNA or other high-molecular fragments with base sequences is applied or adhered directly to the support using an electronic printing or thermal transfer printing.

25. The method of claim 1, wherein the DNA, RNA, PNA or other high-molecular fragments with base sequences solution is directly dropped or injected onto the support.

26. The method of claim 19, wherein the solution of DNA, PNA, RNA or other high-molecular fragments with base sequences is directly dropped or injected onto the support.

27. The method of claim 1, wherein the DNA, RNA, PNA or other high-molecular fragments with base sequences solution is directly dropped onto the support.

28. The method of claim 19, wherein the solution of DNA, PNA, RNA or other high-molecular fragments with base sequences is directly dropped onto the support.

* * * * *